US009456970B2

(12) United States Patent
Rood et al.

(10) Patent No.: US 9,456,970 B2
(45) Date of Patent: *Oct. 4, 2016

(54) DERMATOLOGICAL COMPOSITIONS AND METHODS

(71) Applicant: Upsher-Smith Laboratories, Inc., Maple Grove, MN (US)

(72) Inventors: Gloria A. Rood, Maple Grove, MN (US); Kenneth L. Evenstad, Wayzata, MN (US); Victoria A. O'Neill, Wayzata, MN (US)

(73) Assignee: Upsher-Smith Laboratories, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/851,203

(22) Filed: Sep. 11, 2015

(65) Prior Publication Data
US 2016/0000672 A1 Jan. 7, 2016

Related U.S. Application Data

(60) Continuation of application No. 13/198,928, filed on Aug. 5, 2011, which is a continuation of application No. 12/479,524, filed on Jun. 5, 2009, now Pat. No. 8,013,017, which is a continuation of application No. 10/977,374, filed on Oct. 29, 2004, now abandoned, which is a division of application No. 10/159,562, filed on May 31, 2002, now abandoned.

(60) Provisional application No. 60/295,105, filed on May 31, 2001.

(51) Int. Cl.
| | |
|---|---|
| *A61K 31/19* | (2006.01) |
| *A61K 8/365* | (2006.01) |
| *A61K 8/49* | (2006.01) |
| *A61K 9/00* | (2006.01) |
| *A61K 31/535* | (2006.01) |
| *A61K 31/56* | (2006.01) |
| *A61K 31/573* | (2006.01) |
| *A61K 45/06* | (2006.01) |
| *A61K 47/44* | (2006.01) |
| *A61Q 19/00* | (2006.01) |
| *A61K 8/31* | (2006.01) |
| *A61K 8/34* | (2006.01) |
| *A61K 8/36* | (2006.01) |
| *A61K 8/368* | (2006.01) |
| *A61K 8/73* | (2006.01) |
| *A61K 31/5375* | (2006.01) |

(52) U.S. Cl.
CPC ............... *A61K 8/365* (2013.01); *A61K 8/31* (2013.01); *A61K 8/345* (2013.01); *A61K 8/361* (2013.01); *A61K 8/368* (2013.01); *A61K 8/49* (2013.01); *A61K 8/73* (2013.01); *A61K 9/0014* (2013.01); *A61K 31/19* (2013.01); *A61K 31/535* (2013.01); *A61K 31/5375* (2013.01); *A61K 31/56* (2013.01); *A61K 31/573* (2013.01); *A61K 45/06* (2013.01); *A61K 47/44* (2013.01); *A61Q 19/00* (2013.01); *A61Q 19/007* (2013.01); *A61K 2800/524* (2013.01)

(58) Field of Classification Search
CPC .............................. A61K 8/365; A61K 31/19
See application file for complete search history.

(56) References Cited

U.S. PATENT DOCUMENTS

| | | | |
|---|---|---|---|
| 1,772,975 | A | 8/1930 | Wieland et al. |
| 2,118,566 | A | 5/1938 | Miles |
| 3,227,616 | A | 1/1966 | Van Wessem et al. |
| 3,666,863 | A | 5/1972 | Swanbeck |
| 3,689,668 | A | 9/1972 | Piette |
| 3,806,593 | A | 4/1974 | Swanbeck et al. |
| 3,879,537 | A | 4/1975 | Van Scott et al. |
| 3,920,835 | A | 11/1975 | Van Scott et al. |
| 3,969,396 | A | 7/1976 | Yankee |
| 3,984,566 | A | 10/1976 | Van Scott et al. |
| 3,988,470 | A | 10/1976 | Van Scott et al. |
| 3,991,184 | A | 11/1976 | Kludas et al. |
| 4,021,572 | A | 5/1977 | Van Scott et al. |
| 4,053,630 | A | 10/1977 | Yu et al. |
| 4,067,997 | A | 1/1978 | Kabara |
| 4,105,783 | A | 8/1978 | Yu et al. |
| 4,105,785 | A | 8/1978 | Mauvernay et al. |
| 4,179,271 | A | 12/1979 | Vartanian et al. |

(Continued)

FOREIGN PATENT DOCUMENTS

| | | |
|---|---|---|
| DE | 25 17 413 A1 | 11/1975 |
| DE | 27 44 976 A1 | 4/1979 |
| DE | 32 00 766 A1 | 9/1982 |
| DE | 35 40 175 A1 | 5/1987 |
| DE | 42 21 743 A1 | 1/1994 |
| EP | 0 007 785 A2 | 2/1980 |
| EP | 0 007 785 B1 | 2/1980 |
| EP | 0 042 290 A2 | 12/1981 |
| EP | 0 042 290 B1 | 12/1981 |
| EP | 0 067 513 A2 | 12/1982 |

(Continued)

OTHER PUBLICATIONS

21 C.F.R. §§ 346.1 and 346.10 (1990).

(Continued)

*Primary Examiner* — Samira Jean-Louis
(74) *Attorney, Agent, or Firm* — Mueting, Raasch & Gebhardt, P.A.

(57) ABSTRACT

Dermatological compositions (methods of making and using) that include one or more anesthetic agents and/or one or more anti-inflammatory agents and/or a combination of ammonium, sodium, and potassium salts, preferably of an alpha-hydroxy acid.

20 Claims, No Drawings

(56) References Cited

U.S. PATENT DOCUMENTS

| | | |
|---|---|---|
| 4,194,007 A | 3/1980 | Van Scott et al. |
| 4,197,316 A | 4/1980 | Yu et al. |
| 4,234,599 A | 11/1980 | Van Scott et al. |
| 4,246,261 A * | 1/1981 | Van Scott ............ A61K 9/0014 514/171 |
| 4,252,796 A | 2/1981 | Yu et al. |
| 4,261,969 A | 4/1981 | Heller |
| 4,284,630 A | 8/1981 | Yu et al. |
| 4,285,973 A | 8/1981 | Edwards |
| 4,287,214 A | 9/1981 | Van Scott et al. |
| 4,294,852 A | 10/1981 | Wildnauer et al. |
| 4,316,902 A | 2/1982 | Yu et al. |
| 4,361,571 A | 11/1982 | VanScott et al. |
| 4,363,815 A | 12/1982 | Yu et al. |
| 4,367,224 A | 1/1983 | Van Scott et al. |
| 4,380,549 A | 4/1983 | Van Scott et al. |
| 4,406,896 A | 9/1983 | Higuchi et al. |
| 4,424,234 A | 1/1984 | Alderson et al. |
| 4,478,853 A | 10/1984 | Chaussee |
| 4,507,319 A | 3/1985 | Barratt et al. |
| 4,518,789 A | 5/1985 | Yu et al. |
| 4,540,567 A | 9/1985 | Oneto et al. |
| 4,548,744 A | 10/1985 | Connor |
| 4,588,590 A | 5/1986 | Bernstein |
| 4,593,048 A | 6/1986 | Sato et al. |
| 4,608,370 A | 8/1986 | Aronsohn |
| 4,609,640 A | 9/1986 | Morishita et al. |
| 4,612,331 A | 9/1986 | Barratt et al. |
| 4,626,541 A | 12/1986 | Kaplan |
| 4,649,156 A | 3/1987 | Tanaka et al. |
| 4,654,354 A | 3/1987 | Shroot et al. |
| 4,663,458 A | 5/1987 | Kaplan |
| 4,671,957 A | 6/1987 | Holtshousen |
| 4,678,664 A | 7/1987 | Schmolka |
| 4,704,473 A | 11/1987 | Nakamura et al. |
| 4,715,982 A | 12/1987 | Zabotto et al. |
| 4,740,374 A | 4/1988 | Nakano et al. |
| 4,761,279 A | 8/1988 | Khalil et al. |
| 4,765,922 A | 8/1988 | Contamin et al. |
| 4,783,332 A | 11/1988 | Schreuder |
| 4,794,106 A | 12/1988 | Takashima et al. |
| 4,794,107 A | 12/1988 | Takashima et al. |
| 4,808,322 A | 2/1989 | McLaughlin |
| 4,839,161 A | 6/1989 | Bowser et al. |
| 4,888,354 A | 12/1989 | Chang et al. |
| 4,929,722 A | 5/1990 | Partain, III et al. |
| 4,937,068 A | 6/1990 | Baral |
| 4,983,382 A | 1/1991 | Wilmott et al. |
| 5,002,760 A | 3/1991 | Katzev |
| 5,021,451 A | 6/1991 | McLane et al. |
| 5,028,417 A | 7/1991 | Bhatt et al. |
| 5,057,246 A | 10/1991 | Bertho et al. |
| 5,091,171 A | 2/1992 | Yu et al. |
| 5,093,109 A | 3/1992 | Mausner |
| 5,093,360 A | 3/1992 | Yu et al. |
| 5,100,677 A | 3/1992 | Veech |
| 5,108,751 A | 4/1992 | Hagan et al. |
| 5,110,809 A | 5/1992 | Wang et al. |
| 5,153,230 A | 10/1992 | Jaffery |
| 5,215,759 A | 6/1993 | Mausner |
| 5,254,331 A | 10/1993 | Mausner |
| 5,254,343 A | 10/1993 | Parah et al. |
| 5,258,391 A | 11/1993 | Van Scott et al. |
| 5,262,153 A | 11/1993 | Mishima et al. |
| 5,326,566 A | 7/1994 | Parab |
| 5,341,932 A | 8/1994 | Chen et al. |
| 5,385,938 A | 1/1995 | Yu et al. |
| 5,389,677 A | 2/1995 | Yu et al. |
| 5,391,373 A | 2/1995 | Mausner |
| 5,391,548 A | 2/1995 | Francoeur et al. |
| 5,399,665 A | 3/1995 | Barrera et al. |
| 5,407,958 A | 4/1995 | Heath et al. |
| 5,420,106 A | 5/1995 | Parab |
| 5,420,107 A | 5/1995 | Brooks |
| 5,422,370 A | 6/1995 | Yu et al. |
| 5,444,091 A | 8/1995 | Rapaport et al. |
| 5,446,025 A * | 8/1995 | Lu .................. A61K 9/0014 514/10.3 |
| 5,447,930 A | 9/1995 | Nayak |
| 5,455,033 A | 10/1995 | Silverman et al. |
| 5,470,880 A | 11/1995 | Yu et al. |
| 5,478,489 A | 12/1995 | Fredj et al. |
| 5,478,565 A * | 12/1995 | Geria .................. A61K 9/0043 424/434 |
| 5,480,633 A | 1/1996 | Simion et al. |
| 5,492,935 A | 2/1996 | Yu et al. |
| 5,500,668 A | 3/1996 | Malhotra et al. |
| 5,516,793 A | 5/1996 | Duffy |
| 5,525,345 A | 6/1996 | Warner et al. |
| 5,547,988 A | 8/1996 | Yu et al. |
| 5,550,154 A | 8/1996 | Yu et al. |
| 5,550,158 A | 8/1996 | Yu et al. |
| 5,554,597 A | 9/1996 | Yu et al. |
| 5,554,651 A | 9/1996 | Yu et al. |
| 5,554,652 A | 9/1996 | Yu et al. |
| 5,554,654 A | 9/1996 | Yu et al. |
| 5,556,882 A | 9/1996 | Yu et al. |
| 5,561,153 A | 10/1996 | Yu et al. |
| 5,561,155 A | 10/1996 | Yu et al. |
| 5,561,156 A | 10/1996 | Yu et al. |
| 5,561,157 A | 10/1996 | Yu et al. |
| 5,561,158 A | 10/1996 | Yu et al. |
| 5,561,159 A | 10/1996 | Yu et al. |
| 5,561,166 A * | 10/1996 | Sattler .................. A61K 8/06 514/588 |
| 5,565,487 A | 10/1996 | Yu et al. |
| 5,569,651 A | 10/1996 | Garrison et al. |
| 5,571,837 A | 11/1996 | Yu et al. |
| 5,574,067 A | 11/1996 | Yu et al. |
| 5,578,644 A | 11/1996 | Yu et al. |
| 5,580,902 A | 12/1996 | Yu et al. |
| 5,583,156 A | 12/1996 | Yu et al. |
| 5,589,505 A | 12/1996 | Yu et al. |
| 5,591,774 A | 1/1997 | Yu et al. |
| 5,594,129 A | 1/1997 | Lim et al. |
| 5,594,130 A | 1/1997 | Lim et al. |
| 5,599,843 A | 2/1997 | Yu et al. |
| 5,607,980 A | 3/1997 | McAtee et al. |
| 5,612,376 A | 3/1997 | Yu et al. |
| 5,621,006 A | 4/1997 | Yu et al. |
| 5,637,615 A | 6/1997 | Yu et al. |
| 5,641,475 A | 6/1997 | Yu et al. |
| 5,643,949 A | 7/1997 | Van Scott et al. |
| 5,643,952 A | 7/1997 | Yu et al. |
| 5,643,953 A | 7/1997 | Yu et al. |
| 5,643,961 A | 7/1997 | Yu et al. |
| 5,643,962 A | 7/1997 | Yu et al. |
| 5,643,963 A | 7/1997 | Yu et al. |
| 5,648,388 A | 7/1997 | Yu et al. |
| 5,648,389 A | 7/1997 | Gans et al. |
| 5,648,391 A | 7/1997 | Yu et al. |
| 5,648,395 A | 7/1997 | Yu et al. |
| 5,650,436 A | 7/1997 | Yu et al. |
| 5,650,437 A | 7/1997 | Yu et al. |
| 5,650,440 A | 7/1997 | Yu et al. |
| 5,652,267 A | 7/1997 | Yu et al. |
| 5,654,336 A | 8/1997 | Yu et al. |
| 5,654,340 A | 8/1997 | Yu et al. |
| 5,656,665 A | 8/1997 | Yu et al. |
| 5,656,666 A | 8/1997 | Yu et al. |
| 5,658,580 A | 8/1997 | Mausner |
| 5,665,776 A | 9/1997 | Yu et al. |
| 5,668,177 A | 9/1997 | Yu et al. |
| 5,670,541 A | 9/1997 | Yu et al. |
| 5,670,542 A | 9/1997 | Yu et al. |
| 5,670,543 A | 9/1997 | Yu et al. |
| 5,674,899 A | 10/1997 | Yu et al. |
| 5,674,903 A | 10/1997 | Yu et al. |
| 5,677,339 A | 10/1997 | Yu et al. |
| 5,677,340 A | 10/1997 | Yu et al. |
| 5,681,728 A | 10/1997 | Miao |
| 5,681,853 A | 10/1997 | Yu et al. |
| 5,684,044 A | 11/1997 | Yu et al. |
| 5,686,489 A | 11/1997 | Yu et al. |

(56) References Cited

U.S. PATENT DOCUMENTS

| | | |
|---|---|---|
| 5,690,967 A | 11/1997 | Yu et al. |
| 5,691,378 A | 11/1997 | Yu et al. |
| 5,696,169 A | 12/1997 | Otsu et al. |
| 5,702,688 A | 12/1997 | Yu et al. |
| 5,702,711 A | 12/1997 | Parab |
| 5,703,122 A | 12/1997 | Duffy |
| 5,705,168 A | 1/1998 | Parab |
| 5,707,612 A | 1/1998 | Zofchak et al. |
| 5,709,849 A | 1/1998 | Ito et al. |
| 5,716,992 A | 2/1998 | Yu et al. |
| 5,728,733 A | 3/1998 | Ptchelintsev |
| 5,730,991 A | 3/1998 | Rapaport |
| 5,756,107 A | 5/1998 | Hahn et al. |
| 5,759,557 A | 6/1998 | Epstein et al. |
| 5,760,079 A | 6/1998 | Shaffer et al. |
| 5,776,473 A | 7/1998 | Perricone et al. |
| 5,776,917 A | 7/1998 | Blank et al. |
| 5,804,203 A * | 9/1998 | Hahn ................ A61K 8/19 424/401 |
| 5,807,600 A | 9/1998 | Parab et al. |
| 5,807,890 A | 9/1998 | Yu et al. |
| 5,814,659 A | 9/1998 | Elden |
| 5,814,662 A | 9/1998 | Znaiden et al. |
| 5,827,882 A | 10/1998 | Yu et al. |
| 5,834,510 A | 11/1998 | Yu et al. |
| 5,853,732 A | 12/1998 | Munden |
| 5,856,357 A | 1/1999 | Yu et al. |
| 5,859,723 A | 1/1999 | Jodicke et al. |
| 5,863,943 A | 1/1999 | Groh |
| 5,874,071 A | 2/1999 | Yu et al. |
| 5,876,778 A | 3/1999 | Stewart |
| 5,877,212 A | 3/1999 | Yu et al. |
| 5,882,666 A | 3/1999 | Averill et al. |
| 5,883,128 A | 3/1999 | Yu et al. |
| 5,886,041 A | 3/1999 | Yu et al. |
| 5,886,042 A | 3/1999 | Yu et al. |
| 5,889,054 A | 3/1999 | Yu et al. |
| 5,916,581 A | 6/1999 | Foret et al. |
| 5,922,331 A | 7/1999 | Mausner |
| 5,932,229 A | 8/1999 | Ptchelintsev et al. |
| 5,939,082 A | 8/1999 | Oblong et al. |
| 5,939,457 A | 8/1999 | Miser |
| 5,942,250 A | 8/1999 | Yu et al. |
| 5,942,478 A | 8/1999 | Lopes |
| 5,958,436 A | 9/1999 | Hahn et al. |
| 5,958,975 A | 9/1999 | Yu et al. |
| 5,958,984 A | 9/1999 | Devillez |
| 5,961,996 A | 10/1999 | Garson et al. |
| 5,961,997 A | 10/1999 | Swinehart |
| 5,962,526 A | 10/1999 | Yu et al. |
| 5,990,032 A | 11/1999 | Wu et al. |
| 5,990,109 A | 11/1999 | Chen et al. |
| 6,001,341 A | 12/1999 | Genova et al. |
| 6,022,551 A | 2/2000 | Jampani et al. |
| 6,025,347 A | 2/2000 | Gubernick et al. |
| 6,030,517 A | 2/2000 | Lincot et al. |
| 6,046,238 A | 4/2000 | Yu et al. |
| 6,051,609 A | 4/2000 | Yu et al. |
| 6,054,479 A | 4/2000 | Yu et al. |
| 6,060,512 A | 5/2000 | Yu et al. |
| 6,066,763 A | 5/2000 | Hayakawa |
| 6,069,169 A | 5/2000 | Ptchelintsev et al. |
| 6,139,850 A | 10/2000 | Hahn et al. |
| 6,159,485 A | 12/2000 | Yu et al. |
| 6,174,534 B1 | 1/2001 | Richard et al. |
| 6,174,846 B1 | 1/2001 | Villa |
| 6,180,670 B1 | 1/2001 | Duffy et al. |
| 6,191,167 B1 | 2/2001 | Yu et al. |
| 6,231,840 B1 | 5/2001 | Buck |
| 6,264,963 B1 * | 7/2001 | Leifheit ................ A61K 8/31 424/401 |
| 6,290,943 B1 | 9/2001 | Naser et al. |
| 6,335,023 B1 | 1/2002 | Yu et al. |
| 6,384,079 B1 | 5/2002 | Yu et al. |
| 6,399,082 B1 | 6/2002 | Ganemo |
| 6,403,123 B1 | 6/2002 | Scott et al. |
| 6,416,768 B1 | 7/2002 | Ravaux et al. |
| 6,455,076 B1 | 9/2002 | Hahn et al. |
| 6,461,624 B2 | 10/2002 | Eggers et al. |
| 6,472,356 B2 | 10/2002 | Narula et al. |
| 6,472,432 B1 | 10/2002 | Perricone |
| 6,492,326 B1 | 12/2002 | Robinson et al. |
| 6,710,076 B2 | 3/2004 | Ancira |
| 6,740,327 B2 | 5/2004 | Yu et al. |
| 8,013,017 B2 | 9/2011 | Rood et al. |
| 2001/0016604 A1 | 8/2001 | Yu et al. |
| 2002/0034489 A1 | 3/2002 | Wiegland et al. |
| 2002/0077372 A1 | 6/2002 | Gers-Barlag et al. |
| 2003/0017181 A1 | 1/2003 | Evenstad et al. |
| 2005/0059644 A1 | 3/2005 | Rood et al. |
| 2009/0247632 A1 | 10/2009 | Rood et al. |
| 2011/0288172 A1 | 11/2011 | Rood et al. |

FOREIGN PATENT DOCUMENTS

| | | |
|---|---|---|
| EP | 0 067 513 B1 | 12/1982 |
| EP | 0 086 070 A2 | 8/1983 |
| EP | 0 086 070 B1 | 8/1983 |
| EP | 0 126 348 A2 | 11/1984 |
| EP | 0 152 281 A2 | 8/1985 |
| EP | 0 152 281 A3 | 8/1985 |
| EP | 0 183 527 A2 | 5/1986 |
| EP | 0 183 527 A3 | 5/1986 |
| EP | 0 183 527 B1 | 5/1986 |
| EP | 0 187 433 A1 | 7/1986 |
| EP | 0 225 005 A1 | 6/1987 |
| EP | 0 225 005 B1 | 6/1987 |
| EP | 0 242 967 A1 | 10/1987 |
| EP | 0 242 967 B1 | 10/1987 |
| EP | 0 273 202 A2 | 7/1988 |
| EP | 0 273 202 A3 | 7/1988 |
| EP | 0 413 528 A1 | 2/1991 |
| EP | 0 413 528 B1 | 2/1991 |
| EP | 0 423 929 A1 | 4/1991 |
| FR | 2 456 522 | 1/1981 |
| FR | 2 757 058 A1 | 6/1998 |
| FR | 2 773 074 A1 | 7/1999 |
| FR | 2 795642 A1 | 1/2001 |
| GB | 388513 | 3/1933 |
| GB | 781150 | 8/1957 |
| JP | 59 196823 | 11/1984 |
| JP | 61-207307 | 9/1986 |
| RO | 79428 | 2/1983 |
| WO | WO 85/04101 | 9/1985 |
| WO | WO 02/096374 A2 | 12/2002 |

OTHER PUBLICATIONS

"A Fresh Look at Lactic Acid" *SPC Asia*, Nov. 1997, pp. 21-22 [retrieved on May 26, 2009]. Retrieved from the Internet: <http://www.ingredientstodiefor.com/files/ArticleFreshLookAtLactic.pdf>; 2 pgs.

Ademola et al., "Clinical Evaluation of 40% Urea and 12% Ammonium Lactate in the Treatment of Xerosis," *Am. J. Clin. Dermatol.*, 2002; 3(3): 217-222.

Aggarwal et al., "A Clinical Trial with Cotaryl Cream in Hyperkeratotic Skin Conditions," *Indian J. Dermatol. Venerbol.*, 45(6):442-444 (1979).

*American Academy of Dermatology New Release No. TRN-92*, "Alpha Hydroxy Acids Reduce Wrinkles, Aid in Treating Dry Skin, Acne, Age Spots," American Academy of Dermatology, Evanston, IL, pp. 1-4 (Sep. 15, 1987).

"Antimicrobial Preservatives and Protectants," in Block, *Disinfection, Sterilization, and Preservation*, 4th Ed., Lea & Febiger, Philadelphia, PA, (1991); pp. 883 and 892.

Atkins et al., "Portable, inexpensive instruments to quantify stratum corneum hydration and skin erythema: applications to clothing science" *Dermatol. Online J.*, Dec. 2001; 7(2): 2 [retrieved on May 26, 2009]. Retrieved from the Internet: <http://dermatology.cdlib.org/DOJvol7num2/original/instrumentation/atkins.html>, 15 pgs.

(56) References Cited

OTHER PUBLICATIONS

Barry, "Skin Structure, Function, Diseases, and Treatment," *Dermatological Formulations*, Marcel Dekker, Inc., New York, New York, 1983, pp. 28-29.
Bergwein, "Gesichtsmachen," *Kosmetick*, 16:555-557 (1967).
Billek et al., "Cosmetics for Elderly People," *Cosmetics & Toiletries*, 111:31-37 (Jul. 1996).
Blair, "The Action of a Urea-Lactic Acid Ointment in Ichthyosis," *British Journal of Dermatology*, 94:145-53 (1976).
*Chemical Abstracts*, 85, Nr. 4, Abstract No. 25286r, p. 248 (Jul. 26, 1976).
*Chemical Abstracts*, 103, Nr. 2, Abstract No. 11494k, p. 340 (Jul. 15, 1985).
*Chemical Abstracts*, 103, Nr. 2, p. 1 (Jul. 15, 1985).
*Chemical Abstracts*, 108, Nr. 24, Abstract No. 210190m, p. 367 (Jun. 13, 1988).
Cimino et al., "Ability of Nonenzymic Nitration or Acetylation of *E. coli* Glutamine Synthetase to Produce Effects Analogous to Enzymic Adenylylation," *Proceedings of the National Academy of Sciences*, 66(2):564-571 (1970).
Comstock et al., "Effect of Lactate on Collagen Proline Hydroxylase Activity in Cultured L-929 Fibroblasts," *Proceedings of the National Academy of Sciences*, 66(2):552-557 (1970).
"Current Review of the Alpha-hydroxy Acids," *Skin Therapy Letter*, May 1998; 3(5) [retrieved on Jul. 29, 2004]. Retrieved from the Internet: <http://www.dermatology.org/skintherapy/st10305.html>; 5 pgs.
Darr et al., "Topical Vitamin C Protects Porcine Skin from Ultraviolet Radiation-Induced Damage," *British Journal of Dermatology*, 127:247 -253 (1992).
Davies et al., "Studies on the effect of salicylic acid on normal skin," *British Journal of Dermatology*, 95:187-192 (1976).
Daytona Beach News—Journal. Jul. 2, 2007. "Beat the Clock". Head-to-toe tips for staying Young, pp. 1 D and 3 D.
Denda, Mitsuhiro. "Skin Barrier Function as a Self-Organizing System" 2000. (Review) Forma, 15:227-232.
Ditre, "Cambios cutáneos en mujeres menopáusicas (Skin changes of menopausal women)", *Dermatologia & Cosmetica*, Juan Bravo, Madrid; pp. 1-9 (Mar. 1997).
*Dorland's Illustrated Medical Dictionary—25th Edition*, W.B. Saunders Company, Philadelphia, PA, Title page, publication page and p. 817 (1974).
*Dorland's Illustrated Medical Dictionary—26th Edition*, W.B. Saunders Company, Philadelphia, PA, Title page, publication page and pp. 647, 696, and 697 (1981).
*Dorland's Illustrated Medical Dictionary—27th Edition*, W.B. Saunders Company, Philadelphia, PA, Title page and p. 874 (1988).
*Dorland's Illustrated Medical Dictionary—27th Edition*, W.B. Saunders Company, Philadelphia, PA, Title page and p. 1366 (1988).
Engasser et al., "Cosmetics and dermatology: Bleaching creams," *Journal of the American Academy of Dermatology*, 5(2):143-147 (Aug. 1981).
Fisher, "Allergic Reactions to Topical (Surface) Anesthetics with Reference to the Safety of Tronothane (Pramoxine Hydrochloride)", *CUTIS*, 25:584, 586, 589-591, 625 (Jun. 1980).
Fisher, "The Safety of Pramoxine Hydrochloride When Used as a Topical (Surface) Anesthetic," *CUTIS*, 62:122-123 (1998).
Fredriksson et al., "Urea Creams in the Treatment of Dry Skin and Hand Dermatitis," *Pharmacology and Therapeutics*, 14(6):442-444 (1975).
Freedberg et al., Eds., *Fitzpatrick's Dermatology in General Medicine*, McGraw-Hill, title page, publication page, and pp. 2722-2723 (1999).
Gattefosse, *Formulary of Perfumes and Cosmetics*, Chemical Publishing Co., Inc., New York, NY, p. 204-215 (1959).
Gijsen, "L(+) Lactic Acid and Lactates: Natural Active Ingredients," *Eurocosmetics*, 2 pgs.
Goldemberg, et al., "Correlation of Skin Feel of Emollients to their Chemical Structure," *J. Soc. Cosmet. Chem*, 22:635-54 (1971).
Grice et al., "Urea and Retinoic Acid in Ichthyosis and their Effect on Transepidermal Water Loss and Water Holding Capacity of Stratum Corneum," *Acta Dermatovener (Stockholm)*, 53:114-118 (1973).
Grove et al., "Age-Associated Changes in Human Epidermal Cell Renewal," *Journal of Gerontology*, 38(2):137-142 (1983).
Grove, "Skin Surface Hydration Changes During a Mini Regression Test as Measured In Vivo by Electrical Conductivity," *Current Therapeutic Research*, Oct. 1992; 52(4): 556-561.
Grove et al., "Noninvasive Instrumental Methods for Assessing Moisturizers," *Skin Moisturization*, New York, NY, 2002, pp. 499-528.
Hackh's Chemical Dictionary, 4th Edition, McGraw Hill Book Company, New York, Title page and p. 370 (1969).
Harry, *Harry's Cosmeticology: The Principles and Practice of Modern Cosmetics*, vol. One, 6th Ed., Chemical Publishing Co., Inc., New York, Title page, publication page and chapters 6 and 39 (1973).
Hunt et al., "Anaerobic Metabolism and Wound Healing: An Hypothesis for the Initiation and Cessation of Collagen Synthesis in Wounds," *The American Journal of Surgery*, 135:328-332 (1978).
In Style Magazine, "Beauty You Asked," May 1, 2006, p. 378.
Kabara, "Antimicrobial Agents Derived from Fatty Acids," *JAOCS*, 61(2):397-403 (Feb. 1984).
Kligman et al., "The Anatomy and Pathogenesis of Wrinkles," *British Journal of Dermatology*, 113:37-42 (1985).
Kligman, "Topical Retinoic Acid (Tretinoin) for Photoaging: Conceptions and Misperceptions", *CUTIS*, 57:142-144 (Mar. 1996).
Lavker, "Ammonium Lactate Eases Steroid-Induced Atrophy," *Skin & Allergy News*, p. 2 (Jul. 1991).
Lavker et al., "Changes in Skin Surface Patterns With Age," *Journal of Gerontology*, 35(3):348-354 (1980).
Leyden, "Alpha-Hydroxy Acids 'More than Moisturizers'," *Skin & Allergy News*, p. 30 (Oct. 1991).
*Merck Index: An Encyclopedia of Chemicals, Drugs, and Biologicals*, 11th Edition, Merck & Co., Inc., title page and pp. 130, 131, 363, 896, and 1324 (1989).
Mirkin, "Skin Mysteries," *Health*, 18(1):8 (Jan. 1986).
Moisturizing & Emolliency Documentary, "Unusual Moisturizers and Emollients: Patent Digest for 1966-1977," *Cosmetics and Toiletries*, 93(4):55-60 (Apr. 1978).
Norman, "Causes and Management of Xerosis and Pruritis in the Elderly," *Annals of Long-Term Care*, 9(12):35-40 (Dec. 2001).
Novich et al., "Skin Bleaching Drug Products for Over-the-Counter Human Use; Tentative Final Monograph," *Federal Register: Part V, Department of Health and Human Services*, 47(172):39108-39117 (Sep. 3, 1982).
Orkin et al., Eds., *Dermatology—First Edition*, Prentiss Hall, East Norwalk, Connecticut, title page, publication page and pp. 642-643 (1991).
Osipow, "A Buffering Humectant for Cosmetics," *Drug and Cosmetic Industry*, 88(4):438-9, 508, 510-12, and 514 (1961).
Po, *Non-Prescription Drugs*, Blackwell Scientific Publications, Oxford, title page, publication page and 80-83 (1982).
Rawlings et al., "Stratum Corneum Moisturization at the Molecular Level," *The Journal of Investigative Dermatology*, 103(5):731-740 (Nov. 1994).
Robinson et al., "Dermatitis, Dry Skin, Dandruff, Seborrhea, and Psoriasis Products," *Handbook of Nonprescription Drugs—Seventh Edition*, American Pharmaceutical Association and The National Professional Society of Pharmacists, Washington, D.C., title page, publication page and pp. 561-592 (1982).
Roche Lexikon Medizin, Urban & Schwarzenberg, Munich, Germany, title page, publication page and pp. 895, 971, 980, 1155 (1993).
Rook et al., Eds., *Textbook of Dermatology*, Blackwell Scientific Publications, Oxford, title page, publication page and pp. 2551-2552 (1986).
Rote Liste, Editio Cantor Aulendrof/Württ, Frankfurt, 4 pages (1983).
Sadik, "O-T-C Products for Corns, Calluses, Warts," *Journal of the American Pharmaceutical Association*, NS10(1):8-12 (1970).

(56) References Cited

OTHER PUBLICATIONS

Schmidt et al., "The Pharmacology of Pramoxine Hydrochloride: A New Topical Local Anesthetic," *Current Researches in Anesthesia and Analgesia*, 32(6):418-425 (Nov./Dec. 1953).
Shibasaki et al. "Combined Effects on Antibacterial Activity of Fatty Acids and Their Esters Against Gram-Negative Bacteria", Chapter 2 in Combined Effects on Antibacterial Activity of Fatty Acids and their Esters Against Gram-Negative Bacteria. Shibasaki, Isao; Kato, Nobuyuki. Fac. Eng., Univ. Osaka, Osaka, Japan. pp. 15-24. Publisher: AOCS, Champaign, Ill CODEN:41RBAD Conference; General Review written in English. CAN 91:187184 AN 1979:587184 CAPLUS (Copyright 2003 ACS).
Stern, "Topical Application of Lactic Acid in the Treatment and Prevention of Certain Disorders of the Skin," *The Urologic and Cutaneous Review*, 50(2):106-107 (1946).
"Stubble, Calluses, Veins—Gone, Softened, Hidden," *SHOPETC Magazine*, May 2006, cover page and p. 146.
Terry et al., "Implications of Heavy Chain Disease Protein Sequences for Multiple Gene Theories of Immunoglobulin Synthesis," *Proceedings of the National Academy of Sciences*, 66(2):558-563 (1970).
van der Pol et al., "L(+) Lactates: Multifunctional Cosmetic Ingredients," *Household and Personal Products Industry*, 1998; 35(12): 88-90; 3 pgs. (article).
van Rijsbergen, "L(+)Lactic Acid and Lactates—Natural Moisturizers in cosmetics," *SÖFWI*, Jan. 11, 2000; 126(11): 18-23; 4 pgs. (article).

Van Scott et al., "Alpha hydroxyacids: therapeutic potentials," *The Canadian Journal of Dermatology*, 1(5):108-112 (Nov./Dec. 1989).
Van Scott et al., "Alpha Hydroxy Acids: Procedures for Use in Clinical Practice," *CUTIS (A Yorke Medical Journal)*, 43:222-228 (1989).
Van Scott et al., "Control of Keratinization with α-Hydroxyacids and Related Compounds," *Arch Dermatol*, 110:586-90 (1974).
Van Scott et al., "Dry Skin et cetera, Corneocyte Detachment, Desquamation, and Neo-strata," *International Journal of Dermatology*, 26:90 (Mar. 1987).
Van Scott et al., "Hyperkeratinization, corneocyte cohesion, and alpha hydroxy acids," *Journal of the American Academy of Dermatology*, 11(5):867-879 (Nov. 1984).
Van Scott et al., "Chapter 10—Substances that modify the stratum corneum by modulating its formation," *Principles of cosmetics for the dermatologist*, Frost et al., Eds., The C.V. Mosby Company, St. Louis, MO, title page, publication page and pp. 70-74 (1982).
*Webster's Ninth New Collegiate Dictionary*, Merriam-Webster Inc, Springfield, MA, title page, publication page, and p. 1272 (1983).
Weiss et al., "Topical Tretinoin in the Treatment of Aging Skin," *J. Amer. Acad. of Dermatology*, 19(1):169-175 (1988).
Weiss et al., "Topical Tretinoin Improves Photoaged Skin, A Double-blind Vehicle-Controlled Study," JAMA, Jan. 22/29, 1988, vol. 259, No. 4. pp. 527-532.
Women's Health Magazine, "Women's Health Beauty All-Stars," Jul./Aug. 2007, magazine cover, article cover page, and p. 159.
Yu et al., "Alpha Hydroxy Acids: Science and Therapeutic Use," *Issues and Perspectives of AHAs—Supplement to Cosmetic Dermatology*, pp. 1 and 3 (Oct. 1994).

\* cited by examiner

DERMATOLOGICAL COMPOSITIONS AND METHODS

This application is a continuation application of Ser. No. 13/198,928, filed on Aug. 5, 2011, which is a continuation application of Ser. No. 12/479,524, filed on 5 Jun. 2009, which is a continuation application of Ser. No. 10/977,374, filed on Oct. 29, 2004, which is a divisional application of Ser. No. 10/159,562, filed on 31 May 2002, entitled DERMATOLOGICAL COMPOSITIONS AND METHODS, which claims the benefit of U.S. Provisional Application Ser. No. 60/295,105 filed 31 May 2001, each of which is incorporated by reference, in their entirety.

FIELD OF THE INVENTION

The invention relates to topical compositions that provide dermatological benefit, such as for the treatment of inflammation, itching, pain relief, and/or other conditions associated with skin disorders.

BACKGROUND OF THE INVENTION

Seven dry skin disorders, known as ichthyosis, are often characterized by cracks, flakes, scales, redness, etc. Less severe, but more common, moderate to mild dry skin disorders are often characterized by less severe fissures, chaps, cracks, flakes, redness, etc. Such disorders can also include inflammation and be quite painful. Typically, such disorders are treated with topical oils, hydrating emollients, ointments, etc.

The topical use of alpha-hydroxy and beta-hydroxy acids, alpha-ketoacids, and esters thereof, is well known in the art to be effective as a preventative as well as a therapeutic treatment of dry skin disorders. Treatment is generally effective at acid concentrations of about 1% to about 20% by weight. Skin irritation caused by low pH levels may be ameliorated by neutralizing the acids with a base, such as ammonium hydroxide. See, for example, U.S. Pat. No. 4,105,783 (Yu et al.).

Further, it is believed that skin penetration by such compositions is enhanced using acid/base salts. See, for example, U.S. Pat. No. 4,888,354 (Chang et al.). In addition, the topical compositions may contain additional pharmaceutical and cosmetic additives, provided they do not adversely affect the formulation, stability, and activity of the acids and/or esters. Such additives include, for example, antimicrobials, antibiotics, neoplastic agents, cardiac drugs, antihistamines, anesthetics, antipsychotics, etc. See, for example, U.S. Pat. No. 4,888,354 (Chang et al.), U.S. Pat. No. 5,420,106 (Parab), and U.S. Pat. No. 5,705,168 (Parab).

There is still a need for compositions (e.g., lotions and creams) that can be used to reduce conditions associated with dry skin and other skin disorders, such as inflammation, itching, and/or pain relief.

SUMMARY OF THE INVENTION

One aspect of the present invention combines dermatologically acceptable compositions (i.e., dermatological or dermatologic compositions) with one or more anesthetic and/or anti-inflammatory agents, preferably steroid anti-inflammatory agents. The composition include at least one acid, amide, ester, or salt of an alpha-hydroxy acid, a beta-hydroxy acid, an alpha-keto acid, or combinations thereof (preferably at least one alpha-hydroxy acid, ester, amide, salt thereof, or combinations thereof). More preferably, the compositions include a combination of at least two salts, more preferably, at least one ammonium salt and at least one metal ion salt (preferably sodium or potassium salt) for enhanced penetration of the composition. Preferably, certain compositions include an anti-foaming agent.

A further aspect of the present invention is a composition including at least one alpha hydroxy acid, at least one ammonium salt of an alpha hydroxy acid, at least one potassium salt of an alpha hydroxy acid, and at least one sodium salt of an alpha hydroxy acid.

These compositions can also optionally include topical vehicles such as non-ionic surfactants, thickeners, emollients, humectants, and preservatives to provide preparations, such as lotions, creams, etc., for dry skin having enhanced preventative and therapeutic attributes.

The present invention provides methods for treating a subject, preferably a mammal, and more preferably a human, such as reducing inflammation of the skin, reducing itching and/or pain of the skin, and treating skin disorders that include contacting the skin with compounds containing any of the compositions of the present invention.

Another aspect of the present invention provides methods for preparing the dermatological compositions that include combining at least one acid, amide, ester, or salt of an alpha-hydroxy acid, beta-hydroxy acid, alpha-keto acid, or combinations thereof (preferably at least one alpha-hydroxy acid, ester, amide, salt thereof, or combinations thereof), with one or more anesthetic agents and/or one or more anti-inflammatory agents. Preferably, such methods also include adding one or more ammonium salts and/or one or more metal ion salts. A preferred method of preparing certain dermatological compositions of the present invention includes providing an alpha-hydroxy acid and neutralizing at least a portion of it with ammonium hydroxide in an aqueous solution to provide a neutralized acid solution that preferably may be combined with at least one anti-inflammatory agent and/or at least one anesthetic agent.

A further method of preparing a dermatologic composition of the present invention includes combining at least one alpha-hydroxy acid, beta-hydroxy acid, or alpha-keto acid, or combinations thereof, with at least one ammonium salt of an alpha-hydroxy acid, beta-hydroxy add, or alpha-keto acid, or combinations thereof, at least one sodium salt of an alpha hydroxy acid, beta-hydroxy acid, or alpha-keto acid, or combinations thereof and at least one potassium salt of an alpha hydroxy acid, beta-hydroxy acid, or alpha-keto acid, or combinations thereof. Preferably, the method includes combining at least one alpha-hydroxy acid, beta-hydroxy acid, or alpha-keto acid, or combinations thereof, with at least two of the above ammonium, sodium, and potassium salts.

High concentrations, such as from about 10% to about 30% by weight, of alpha-hydroxy acids in a skin preparation, when neutralized to yield the ammonium salts, have been found to develop an unpleasant odor and occasionally may result in yellow coloration over time. Thus, the present invention also provides a method for preparing such compositions using activated charcoal for deodorizing. Compositions of the invention may be contacted with activated charcoal. Thereafter, the charcoal may be separated from the composition. Compositions that may be contacted with the activated charcoal may include compositions that have been neutralized with ammonium hydroxide. Deodorizing is defined as removing or significantly reducing a fragrance by neutralization or adsorption. Odor-free is defined as a fragrance completely or substantially eliminated from a composition.

DETAILED DESCRIPTION OF PREFERRED EMBODIMENTS OF THE INVENTION

The invention concerns dermatological compositions that can be in the form of dermatologically acceptable lotions and creams, for example. The compositions of the present invention can be used to treat one or more skin disorders, such as dry skin, ichthyosis, inflammation, and irritation. Certain preferred compositions can be used to reduce the amount of inflammation of the skin of a human. Certain other preferred compositions can be used to reduce the amount of itching and/or pain of the skin of a human. Certain other preferred compositions include a combinations of salts that enhance skin penetration of the active ingredients of the compositions.

Acids, Amides, Esters, Salts

The dermatological compositions include at least one active ingredient selected from an acid, amide, ester, or salt. Preferably, such active ingredients are racemic mixtures and, preferably, are selected from the group of an alpha-hydroxy acid, a beta-hydroxy acid, an alpha-keto acid, an ester thereof, an amide thereof, a salt thereof, and combinations thereof. More preferably, such active ingredients are selected from the group of an alpha-hydroxy acid, an amide thereof, an ester thereof, a salt thereof, and combinations thereof. Certain preferred embodiments include a combination of at least one alpha-hydroxy acid and at least one salt thereof. Preferably the salt is an ammonium salt, a metal ion salt (e.g., a potassium salt or a sodium salt), or a combination thereof. More preferably, a combination of such salts is used. Even more preferably, at least two different salts are used. Most preferably, a combination of an ammonium salt, a potassium salt, and a sodium salt is used.

Examples of such acids, amides, esters, or salts include citric acid, glycolic acid, glucuronic acid, galacturonic acid, alpha-hydroxybutyric acid, alpha-hydroxyisobutyric acid, beta-hydroxybutyric acid, lactic acid, malic acid, mandelic acid, mucic acid, pyruvic acid, saccharic acid, tartaric acid, tartronic acid, maleic acid, beta-phenyllactic acid, beta-phenylpyruvic acid, glucuronolactone, gluconolactone, methyl pyruvate, ethyl pyruvate, salts thereof, and combinations thereof.

A preferred set of such active ingredients includes the alpha-hydroxy acids. Alpha-hydroxy acids are aliphatic mono- and di-carboxylic acids including, but not limited to, citric acid, glycolic acid, glucuronic acid, galacturonic acid, alpha-hydroxybutyric acid, alpha-hydroxyisobutyric acid, lactic acid, malic acid, mandelic acid, mucic acid, pyruvic acid, saccharic acid, tartaric acid, tartonic acid, and the like. Preferred alpha-hydroxy acids of the present invention are those of the formula (I): R—CH(OH)—COOH, wherein R is an alkyl group or a hydrogen. Preferably, R is a $C_1$ to $C_5$ alkyl group including, for example, methyl, ethyl, propyl, butyl, or pentyl as well as branched groups thereof. Preferred acids include lactic, glycolic, and malic acids. Most preferred is lactic acid.

Typically, the compositions include both an acid and a salt thereof, as for example, an alpha-hydroxy acid and an ammonium salt thereof. The alpha-hydroxy acids and a base, such as ammonium hydroxide, me typically reacted in an aqueous solution to provide a neutralized acid solution. Generally, at least a portion of the acid is neutralized. Thus, as used herein, a "neutralized" acid solution or combination of acids in solution is defined as an acid solution in which at least a portion of the acid is neutralized to provide the salt of the acid or acids. The neutralized acid solution, formed when an acid is reacted with an ammonium-containing base, such as ammonium hydroxide, can be generally free of unreacted ammonia (herein "unreacted ammonia" refers to dissolved ammonium ions). This may occur when a stoichiometrically lesser amount of the base is added to the acid. A neutralized acid solution, as defined herein, may also include solutions in which unreacted ammonia is present.

The compositions preferably include one or more acids, amides, esters, or salts present in a total amount (e.g., acid plus salt) of at least about 1% by weight, more preferably at least about 5% by weight, and even more preferably at least about 8% by weight, based on the total weight of the composition (e.g., lotion, cream, etc.). Additionally, the one or more acids, amides, esters, or salts are present in the compositions in a total amount no greater than about 50% by weight, more preferably, no greater than about to about 40% by weight, and even more preferably no greater than about 15%, based on the total weight of the composition. Typically, one or more acids, in the form of a fee acid, in combination with one or more salts are present in the compositions. Preferably, the total amount of one or more free acids is at least about 1% by weight, and more preferably, at least about 10% by weight, based on the total weight of the composition. Preferably, the total amount of one or more free acids is no greater than about 30% by weight, more preferably, no greater than about 20% by weight, and most preferably no greater than about 15% by weight, based on the total weight of the composition. Preferably, the total amount of one or more salts is at least about 1% by weight, and more preferably, at least about 5% by weight, based on the total weight of the composition. Preferably, the total amount of one or more salts is no greater than about 40% by weight, and more preferably, no greater than about 30% by weight, based on the total weight of the composition. The pH of the compositions of the present invention are preferably at least about 3, and more preferably at least about 4.5, and preferably no greater than about 6, and more preferably no greater than about 5.5.

In certain preferred embodiments, the compositions include a combination of one or more ammonium salts, one or more potassium salts, and one or more sodium salts. Even more preferably, the compositions include a combination of 2 or more salts. In such compositions, preferably, the total amount of ammonium salts, if present, (preferably, of one or more alpha-hydroxy acids) is at least about 1% by weight, and more preferably, at least about 5% by weight, based on the total weight of the composition. Preferably, the total amount of ammonium salts, if present, (preferably, of one or more alpha-hydroxy acids) is no greater than about 40% by weight, and more preferably, no greater than about 30% by weight, based on the total weight of the composition. Most preferably, the ammonium salt is ammonium lactate and, if present, is present in an amount of, preferably at least about 10% and more preferably at least about 15.9%, and preferably no greater than about 29.6%, even more preferably no greater than about 15%, based on the total weight of the composition. In such compositions, preferably, the total amount of potassium salts, if present, (preferably, of one or more alpha-hydroxy acids) is at least about 1% by weight, and more preferably, at least about 5% by weight, based on the total weight of the composition. Preferably, the total amount of potassium salts, if present, (preferably, of one or more alpha-hydroxy acids) is no greater than about 30% by weight, and more preferably, no greater than about 20% by weight, based on the total weight of the composition. Most preferably, the potassium salt is potassium lactate and, if present, is present in an amount of at least about 3% and no greater than about 7%, based on the total weight of the composition. In such compositions, preferably, the total amount of sodium salts, if present, (preferably, of one or more alpha-hydroxy acids) is at least about 1% by weight, and more preferably, at least about 5% by weight, based on the total weight of the composition. Preferably, the total amount of sodium salts, if present, (preferably, of one or mom alpha-hydroxy acids) is no greater than about 30% by weight, and more preferably, no greater than about 20% by weight, based on the total weight of the composition. Most preferably, the sodium salt is preferably sodium lactate and, if present, is present in an amount of about 3% and no greater than about 7%, based an the total weight of the composition.

Anesthetic Agents and/for Anti-Inflammatory Agents

Certain preferred compositions may additionally include one or more anesthetic agents and/or anti-inflammatory agents to provide enhanced therapeutic benefits to the skin preparation. Typically, an anti-inflammatory agent will reduce, and preferably, eliminate, inflammation of the skin of a subject when the composition is applied topically. Typically, an anesthetic agent will reduce, and preferably, eliminate, itching and/or pain of the skin of a subject when the composition is applied topically. Various combinations of such agents can be used for desired effect.

Anesthetic agents that can be used in the present invention include topical local anesthetics, such as anesthetics that can be used topically on the skin or can be injected as a local anesthetic. Examples of such topical local anesthetic agents include, but are not limited to, pramoxine HCl, benzocaine, benzyl alcohol, dibucaine HCl, dyclonine HCl, lidocaine, tetracaine, and tetracaine HCl. Combinations of such agents can be used. A preferred anesthetic agent is pramoxine HCl.

Preferably, the total amount of one or more anesthetic agents, if present, is at least about 0.5% and more preferably at least about 0.75%, based on the total weight of the composition. Preferably, the total amount of one or more anesthetic agent is no greater than about 20%, and more preferably, no greater than about 5%, based on the total weight of the composition.

Anti-inflammatory agents that can be used in the present invention include steroids (i.e., corticosteroids). Examples of such agents include, but are not limited to, hydrocortisone acetate, betamethasone dipropionate, amcinonide, betamethasone valerate, fluocinolone acetonide, triamcinolone acetonide, clocortolone pivalate, and dexamethasone. Combinations of such agents can be used. A preferred steroid for use in the present invention is hydrocortisone acetate.

Preferably, the total amount of one or more anti-inflammatory agents, if present, is at least about 0.01%, and more preferably, at least about 0.05% by weight, based on the total weight of the composition. Preferably, the total amount of one or more anti-inflammatory agent is no greater than about 2.5%, and more preferably, no greater than about 1.5% by weight, based on the total weight of the composition.

Anti-Foaming Agents

Anti-foaming agents, or foam depressants, are optionally added to the compositions of the present invention to prevent undesirable creaming upon application of the composition when rubbed into the skin. "Creaming" is understood by those skilled in the mat to occur when a composition rubbed into the skin forms a white layer on the skin before penetration. The more vigorously the composition is rubbed, the whiter the composition becomes. It has been discovered that by adding an anti-foaming agent to a dermatological composition, creaming is substantially eliminated. Although not caused exclusively by anesthetic agents, creaming may occur when one or more topical anesthetic agents, particularly pramoxine HCl, is present in the composition. Pramoxine HCl is a desirable anesthetic agent as compared with other anesthetics, such as lidocaine and benzocaine, because many people have allergies to these other anesthetics. Pramoxine HCl does not cause the same topical sensitivity as compared to these other anesthetics, it is effective at minimal concentrations, and has a duration of action longer than that of other anesthetics (see, for example, Fisher, A. F.; "The Safety of Pramoxine Hydrochloride When Used as a Topical (Surface) Anesthetic," *Cutis,* 62:122-123 (1998); Fisher, A. A.; "Allergic Reactions to Topical (Surface) Anesthetics with Reference to the Safety of Tronothane," *Cutis,* 25:584 (1980); and Schmidt, J. L., Blockus, L. E., Richards, R. K., "The Pharmacology of Pramoxine Hydrochloride: A New Topical Anesthetic," *Anesth. Analg.,* 32:418 (1953)), but it does have the undesirable side-effect of causing creaming upon application to the skin when used in the compositions of the present invention. This problem is solved by including an anti-foaming agent in the compositions of the present invention.

Acceptable anti-foaming agents of the present invention include silicone-based oils, preferably dimethylsiloxane polymers, and copolyol waxes. Such dimethylsiloxane polymers are commercially available under the trade designations DIMETHICONE 250, DIMETHICONE 350, DIMETHICONE 450, CYCLOMETHICONE, and DIMETHICONE, all from Dow Corning, Midland, Mich. A particularly preferred anti-foaming agent is DIMETHICONE 350 dimethylsiloxane polymer. Combinations of such agents can be used. Effective concentrations of DIMETHICONE 350 from Dow Corning, Midland, Mich., or other anti-foaming agents in the compositions of the present invention, if present, are at least about 0.25% by weight, more preferably at least about 0.5% by weight, and most preferably at least about 0.8% by weight. Preferably, the compositions include no greater than about 3% by weight, more preferably no greater than about 2% by weight, and most preferably no greater than about to about 1.2% by weight.

Non-Ionic Surfactants

Non-ionic surfactants are present in preferred formulations to aid in providing an emulsion of the composition. Selection of surfactant and concentration of the surfactant will have a significant effect on the overall "feel" of the composition. Also, a greater stability of the composition may be gained through the blending of multiple non-ionic surfactants than may be achieved through the use of any single surfactant. Preferred non-ionic surfactants that may be used in the compositions of the present invention include glyceryl stearate, PEG 100-stearate, polyoxyl-20-cetostearyl ether, glyceryl monooleate, glyceryl palmitostearate, self-emulsifying wax, polyoxyl-20-stearate, polyoxyl-40-stearate, polyoxyl-60-stearate, polyoxyl-80-stearate, polyoxyl-20-oleate, polyoxyl-40-oleate, polyoxyl-60-oleate, polyoxyl-80-oleate, polyoxyl-20-palmitate, polyoxyl-40-palmitate, polyoxyl-60-palmitate, polyoxyl-80-palmitate, laureth-2, laureth-4, laureth-6, and laureth-8. More preferred non-ionic surfactants include emulsifying wax, such as POLAWAX (available from Croda, Parsippany, N.J.), laureth-4, and polyoxyl-40-stearate. A most preferred non-ionic surfactant is self-emulsifying wax.

Combinations of such agents can be used such as a combination is glyceryl stearate and PEG-100 stearate. A preferred non-ionic surfactant of the present invention includes a system of glyceryl stearate, PEG-100 stearate, polyoxyl-40-stearate, and laureth-4. Glyceryl stearate and PEG-100 stearate are supplied pre-blended by Uniqema (formerly ICI Americas. New Castle Del.). Effective concentrations of the pre-blended glyceryl stearate and PEG-100 stearate in the compositions of the present invention are at least about 2.0% by weight, and more preferably at least about 2.75% by weight, based on the total weight of the composition. Preferably, compositions of the present invention contain no greater than about 5.5% by weight, and more preferably no greater than about to about 5.25% by weight, based on the total weight of the composition. Polyoxyl-40-stearate is selected because the stearates tend to enhance composition stability in comparison to the oleates and palmitates. Polyoxyl-40-stearate is available in cosmetic grade from Uniqema (New Castle. Del.). Effective concentrations of polyoxyl-40-stearate in the compositions of the present invention are preferably at least about 0.5% by weight, and more preferably at least about 0.75% by weight, based on total weight of the composition. Preferably, effective concentrations of polyoxyl-40-stearate in the compositions of the present invention are no greater than about 5% by weight, and more preferably no greater than about 1.25% by weight, based on total weight of the composition. Effective concentrations of laureth-4 in the compositions of the present invention are preferably at least about 0.5% by weight, and more preferably at least about 1.25% by weight, based on total weight of the composition. Effective concentrations of laureth-4 in the compositions of the present invention are preferably no greater than about 3%, and more preferably no greater than about 1.75% by weight, based on total weight of the composition. Effective concentrations of emulsifying wax in preferred compositions of the present invention are preferably at least about 2% and preferably no greater than about 10%, based on the total weight of the composition.

Thickeners

Although the non-ionic surfactants impart a certain amount of thickening to the compositions of the present invention, it is difficult to find the correct balance of surfactants and concentrations thereof that will impart the desired stability to the composition. Therefore, thickeners, also known in the art as viscosity modifiers, are preferably used to adjust the composition to the desired consistency without affecting the stability imparted by the non-ionic surfactant system. Acceptable thickeners that may be used in the compositions of the present invention include methyl cellulose, hydroxypropyl methyl cellulose, ethyl cellulose, cetyl alcohol, cetostearyl alcohol, stearyl alcohol, magnesium aluminum silicate, xanthan gum, aluminum magnesium silicate, tribeneonite, kaolin, magnesium trisilicate, monemorillonite, saeonite, stearic acid, and talc. Combinations of such agents can be used.

A preferable thickener of the present invention includes a system of methyl cellulose, cetyl alcohol, and magnesium aluminum silicate. Magnesium aluminum silicate is particularly preferred element of the thickener system as it acts as both an emulsion stabilizer as well as a viscosity modifier. It also imparts to the composition a smooth, silky, slippery feel without affecting the stability of the composition contributed by the non-ionic surfactant system and does not interfere with the creaming prevention of the anti-foaming agent. Effective concentrations of methyl cellulose in the compositions of the present invention are preferably at least about 0.0001% by weight, and more preferably at least about 0.0005% by weight, based on total weight of the composition. Effective concentrations of methyl cellulose in the compositions of the present invention are preferably no greater than about 1% by weight, and more preferably no greater than about 035% by weight, based an total weight of the composition. Effective concentrations of cetyl alcohol in the compositions of the present invention are preferably at least about 0.2% by weight, and mare preferably at least about 0.5% by weight, based on total weight of the composition. Effective concentrations of cetyl alcohol in the compositions of the present invention are preferably no greater than about 5% by weight, and more preferably no greater than about 3.25% by weight, based on total weight of the composition. Effective concentrations of magnesium aluminum silicate in the compositions of the present invention are preferably at least about 0.5% by weight, more preferably at least about 1% by weight, and most preferably at least about 1.25% by weight, based on total weight of the composition. Effective concentrations of magnesium aluminum silicate in the compositions of the present invention me preferably no greater than about 10% by weight, more preferably no greater than about 5% by weight, and most preferably no greater than about 1.75% by weight, based on total weight, of the composition.

An additional preferred thickener of compositions of the present invention includes stearic acid. In these preferred compositions thickened using stearic acid, the stearic acid is preferably present in an amount of at least about 3% and no greater than about 5%, based on total weight of the composition.

Emollients and Humectants

Emollients and humectants soften the skin and stabilize and control the moisture content of a dermatological composition. Preferred emollients that may be used in the compositions of the present invention include glycerin 995%, glycerin 95%, glycerin 85%, cetyl alcohol, light mineral oil, medium mineral oil, and heavy mineral oil. Preferred humectants that may be used in the compositions of the present invention include glycerin 99.5%, glycerin 95%, glycerin 85%, propylene glycol, and butylene glycol. Combinations of such agents can be used.

More preferable emollients and humectants of the present invention include glycerin 99.5%, propylene glycol, and light mineral oil. Glycerin 99.5% and propylene glycol, when used together, typically act synergistically to aid in stabilizing compositions of the present invention. Further, propylene glycol enhances penetration of the skin by compositions at concentrations of 5% by weight or more, based on total weight of the composition. Conversely, butylene glycol used alone is not a penetration enhancer, but does work synergistically with glycerin 99.5% to enhance penetration. Effective concentrations of glycerin 99.5% in the compositions of the present invention are preferably at least about 1% by weight, more preferably at least about 3% by weight, and even more preferably at least about 3.75% by weight, based on total weight of the composition. Effective concentrations of glycerin 99.5% in the compositions of the present invention are preferably no greater than about 10% by weight, more preferably no greater than about 6% by weight, and even more preferably no greater than about 4.25% by weight, based on total weight of the composition. Effective concentrations of propylene glycol in the compositions of the present invention am preferably at least about 1% by weight, and more preferably at least about 3% by weight, based on total weight of the composition. Effective concentrations of propylene glycol in the compositions of the present invention are preferably no greater than about 15% by weight, and more preferably no greater than about 10% by weight, based on total weight of the composition.

Light mineral oil is preferable as an emollient as it imparts less of a greasy feel to the composition, giving it a lighter feel than do the heavier oils. Effective concentrations of light mineral oil in the compositions of the present invention are preferably at least about 1% by weight, more preferably at least about 3% by weight, even more preferably at least about 4% by weight, and most preferably at least about 5% by weight, based on total weight of the composition. Effective concentrations of light mineral oil in the compositions of the present invention are preferably no greater than about 20% by weight, more preferably no greater than about 15% by weight, and most preferably no greater than about 12% by weight, based on total weight of the composition.

Preservatives

Preservatives prolong the useful life of the composition by killing bacteria, yeasts, and molds which may impair the effectiveness of the compositions of the present invention. Preferable preservatives that may be used in the compositions of the present invention include methylparaben, ethylparaben, propylparaben, propylparaben potassium salt, propylparaben sodium salt, and butylparaben. Combinations of such agents can be used. More preferable preservatives of the present invention include methylparaben and propylparaben. Methyl and propylparaben attack water-bourne microbes, and when used together, their effectiveness is greater than each used alone. Effective concentrations of methylparaben in the compositions of the present invention are preferably at least about 0.02% by weight, and more preferably at least about 0.1% by weight, based on total weight of the composition. Effective concentrations of methylparaben in the compositions of the present invention are preferably no greater than about 1% by weight, more preferably no more than about 0.3% by weight, and even more preferably no greater than about 0.2% by weight, based on total weight of the composition. Effective concentrations of propylparaben in the compositions of the present invention are preferably at least about 0.01% by weight, more preferably at least about 0.025% by weight, and even more preferably at least about 0.1%, based on total weight of the composition. Effective concentrations of propylparaben in the compositions of the present invention are preferably no greater than about 1% by weight, more preferably no greater than about 0.6% by weight, and even more preferably no greater than about 0.075% by weight, based on total weight of the composition.

Fragrance

If desired, a component may be added to the composition to impart a fragrance. Fragrances may be used to add a pleasing scent to a generally unscented composition or, alternatively, may be used to assist in concealing the odor of a composition having a strong and/or unpleasant scent. Fragrance components, if included in a preferred composition, are preferably present in the compositions in an amount of no greater than about 1% by weight, based on the total weight of the composition.

Water, preferably purified water, is typically and preferably used in the compositions of the invention. Water may be used in any amount required to prepare the compositions of the invention, but is typically present in an amount of at least about 30% and typically no greater than about 60% by weight, based on the total weight of the composition.

Methods of Preparation

An acid/acid salt solution is made by mixing a selected alpha-hydroxy, beta-hydroxy, alpha-keto acid, an ester, amide, or salt thereof, an ammonium salt, a metal ion salt, or a combination of any of the above, with purified water or by neutralizing an acid with a stoichiometrically lesser amount of base, such as ammonium hydroxide, to form the "neutralized" acid/acid salt solution. Alternatively, a commercially available salt, such as an ammonium lactate solution (available from PURAC America, Lincolnshire, Ill., or Pfanstiehl Labs, Inc., Waukegan, Ill.) may be combined with an acid to form an acid/acid salt solution.

A Gum Phase composition is preferably prepared by mixing a thickener and, optionally, fillers, into hot, purified water, mixing until uniform at a temperature of about 80° C. to about 85° C. A Water Phase composition is preferably prepared using hot purified water, optionally including emulsifiers, humectants, lubricants, thickeners, and antimicrobial agents. The Gum Phase is typically transferred to the Water Phase and mixed, maintaining a temperature of about 80° C. to about 85° C. An Oil Phase composition is preferably prepared by mixing mineral oil with, optionally, one or more of a surfactant, a lubricant, an emulsifier, a foam stabilizer and an emollient. The Oil Phase is typically heated to about 80° C. to about 85° C. An Active Phase composition is preferably prepared by dissolving and mixing one or more of an anesthetic agent and/or an anti-inflammatory agent with purified water.

The Oil Phase is typically added to the Water Phase, mixed, and cooled. To this, preferably, the acid/acid salt composition is added, with mixing, and to this the Active Phase is preferably added, with continued mixing. The pH of the resulting composition is adjusted to the desired level using either base or acid, and any desired optional agents, such as anesthetics or anti-inflammatory agents, are then added to the composition, as disclosed in the Examples.

Deodorized Compositions

One of the problems associated with neutralizing the alpha-hydroxy acid with ammonium hydroxide is that in the reaction product, free or unreacted ammonia is present. In dermatological preparations, such as lotions and creams, that contain low concentrations of reactive product, the unreacted ammonia is not often noticeable nor objectionable. At higher concentrations of the reactive product, however, such as neutralized alpha-hydroxy acid greater than 10% by weight, unreacted ammonia from the dermatological preparations can give off a strong, unpleasant ammonia odor. Currently available products having a high percentage of unreacted ammonia employ fragrances to mask the unpleasant odor of ammonia. A disadvantage to the use of fragrances to mask the odor is that many patients who require treatment with high concentrations of alpha-hydroxy acids are at the same time allergic to such fragrances and may experience irritation and stinging. Often the diseased skin becomes abraded or broken. Use of fragrances in products applied to the skin may result in unpleasant side effects. A further problem associated with high concentrations of the neutralized alpha-hydroxy acids is that the preparations occasionally develop a yellow coloration over time.

In order to prepare a deodorized composition of the present invention, the alpha-hydroxy acid is combined with ammonium hydroxide, to provide a neutralized acid solution containing unreacted ammonia. Before combining the neutralized acid solution, containing unreacted ammonia, with the selected anesthetic and/or anti-inflammatory agents or other ingredients, the reaction product is contacted with activated carbon. The activated carbon purifies, decolorizes, and removes odor from the composition by absorbing unreacted ammonia, and other impurities that may be present in the composition, onto the surface of the carbon particles. The deactivated carbon has an extremely large surface area per unit weight making it an efficient absorptive material. The 'activation' of carbon in its manufacture produces many pores within the carbon particles. It is the vast area of the walls within these pores that accounts for most of the total surface area of the carbon.

Activated carbon adsorption is a time-release phenomenon that takes place in three steps. Initially, impurities in solution contact the external surface of a carbon particle as the liquid passes through the carbon bed. Secondly, impurities diffuse into the pores of the carbon particle. Finally, impurities are attracted to the pore wall and held by electrostatic (physical) or chemical forces. The adsorption method required to deodorize the compositions of the present invention is dependent on contact time with the carbon, unreacted ammonia concentration, impurity concentration, and adsorption affinity.

Deodorizing methods of the present invention preferably include passing the neutralized solution, containing unreacted ammonia, through an activated carbon cartridge to provide a deodorized filtrate. The filtrate is then typically combined with one or more anesthetic agents described above and/or one or more anti-inflammatory agents described above, providing a composition for use in dermatological formulations.

Methods of the present invention alternatively include forming a slurry of activated carbon particles and neutralized acid solution containing unreacted ammonia, which is then filtered to provide the deodorized composition of the present invention. A preferred method for large scale commercial preparation involves adding activated carbon to the neutralized solution to form a slurry which is stirred prior to filtering. The amount of activated carbon necessary in the method of the present invention may vary from about 30% to about 75% by weight of the total aqueous solution of the neutralized alpha-hydroxy acid. The slurry of the activated carbon and neutralized acid is stirred at ambient temperatures for about 15 minutes to about 2 hours. Following this treatment, the carbon is filtered off and the deodorized filtrate is combined with the selected anesthetic and/or anti-inflammatory agents.

Optional Additives

The resulting composition is used to prepare dermatological formulations in the form of, for example, creams and lotions, in accordance with well known procedures. Such formulations are well known to those of skill in the art. Examples of additives, as indicated above, which may be used in formulating creams include, but are not limited to, petrolatum, non-ionic surfactants, mineral oil, long-chain alcohols, and fatty acids. Examples of additives used in formulating lotions include, but are not limited to, propylene glycol and non-ionic surfactants.

EXAMPLES

Objects and advantages of this invention are further illustrated by the following examples, but the particular materials and amounts thereof recited in these examples, as well as other conditions and details, should not be construed to unduly limit this invention.

Examples 1-4

Preparation of Compositions Containing Anti-Inflammatory and/or Anesthetic Agents Four preferred formulations, Formulations A-D, of a moisturizing cream are listed in Table 1. These compositions were made using the following procedure:

Ammonium Lactate Solution

A 50.70% ammonium lactate solution was purchased from Pfanstiehl Labs (Waukegan, Ill.) or PURAC America (Lincolnshire, Ill.).

Gum Phase Preparation

A portion of the purified water was measured into a jacketed kettle. The water was haled to about 80° C. to about 85° C. and mixed. With continued mixing, the magnesium aluminum silicate, NF (Vanderbilt, Norwalk Conn.) and methyl cellulose, USP, (Dow Chemical, Midland, Mich.) were added to the water. The Gum Phase was mixed for at least 45 minutes, until uniform, while maintaining a temperature of about 80° C. to about 85° C.

Water Phase Preparation

To a jacketed compounding kettle the following ingredients were added using a transfer pump: hot purified water, USP, and glycerin, 99.5%, USP (Dow Chemical, Midland, Mich.). The transfer pump was rinsed with additional purified water. The Water Phase was mixed. The Gum Phase was transferred to the Water Phase using a transfer pump fitted with a 60 mesh screen. The Gum Phase kettle was rinsed with additional hot purified water, USP. The Water Phase and Gum Phase mixture was mixed for at least about 15 minutes while adjusting the temperature to about 80° C. to about 85° C. The methylparaben (Napp Technologies, Saddlebrook, Ill.) was added. The Water/Gum Phase was mixed for about 20 minutes to about 35 minutes while maintaining a temperature of about 80° C. to about 85° C.

Oil Phase Preparation

To a jacketed compounding kettle the following ingredients were added:
light mineral oil, NF (Penreco, Karns City, Pa.), propylene glycol, USP (Dow Chemical, Midland, Mich.), laureth-4 (Uniqema, New Castle, Del.), a glyceryl stearate and PEG-100 stearate blend (Uniqema. New Castle, Del.), polyoxyl-40-stearate, NF (Uniqema, New Castle, Del.), cetyl alcohol, NF (Croda, Parsippany, N.J.), DIMETHICONE 350 (Dow Corning, Midland, Mich.), and propylparaben, NF (Napp Technologies, Saddlebrook, Ill.). The Ingredients were mixed and heated to about 80° C. to about 85° C.

Active Phase Preparation

Into a compounding kettle purified water, USP, was weighed out. The pramoxine HCl, USP (Abbott Labs, Waukegan, Ill.) was added to the water. The solution was mixed until the pramoxine HCl was dissolved.

Emulsion Phase

When the temperatures of the water and oil phases were about 80° C. to about 85° C. the oil phase was added to the water phase using a transfer pump. The emulsion was mixed for at least about 30 minutes. The emulsion was cooled with ambient water while mixing until the batch temperature reached was about 45° C. to about 50° C. When this temperature was reached, the ammonium lactate solution was added using a transfer pump. The pump was rinsed with purified water, USP. Active vacuum was applied to the emulsion at about 12 inches Hg. to about 14 inches Hg. Cooling and mixing continued until the emulsion reached about 39° C. to about 41° C. The vacuum was released and the active phase was added using a transfer pump with continued mixing. The transfer pump was rinsed with additional purified water, USP. Active vacuum was applied at about 12 inches Hg to about 14 inches Hg. (about 0.40 atm. to about 0.47 atm.) while cooling continued until a product temperature of about 37° C. was reached. When the batch reached about 37° C., vacuum was released, the cooling water drained from kettle jacket and steam applied to jacket for about 60 seconds to about 90 seconds to relieve emulsion plating on the kettle walls. The vacuum was reapplied at about 12 inches Hg to about 14 inches Hg. (about 0.40 atm. to about 0.47 atm). Ambient cooling water was reapplied to the jacket and the batch was cooled to about 35° C.

pH Adjustment

A sample of the emulsion was removed. The pH was measured. If it was within about 45 to about 5.5, the batch was complete. If the pH was not within this range, either strong ammonia solution was added to increase the pH or lactic acid, USP was added to decrease the pH. Mixing was continued while the pH was adjusted.

TABLE 1

Percentages by weight

| Ingredient | Formula A | Formula B | Formula C | Formula D |
|---|---|---|---|---|
| Purified Water, USP | 45.80 | 45.80 | 44.80 | 45.9 |
| Methylparaben, NF | 0.15 | 0.15 | 0.15 | 0.15 |
| Glycerin, 99%, USP | 4.00 | 4.00 | 4.00 | 4.00 |
| Methyl cellulose, NF | 0.001 | 0.001 | 0.001 | 0.001 |
| Magnesium Aluminum Silicate, NF | 1.5 | 1.50 | 1.50 | 1.50 |
| Light Mineral Oil, NF | 10 | 10.00 | 10.00 | 10.00 |
| Propylene Glycol, USP | 5.00 | 5.00 | 5.00 | 5.00 |
| Glyceryl Stearate (and) PEG-100 Stearate (pre-blended) | 5.00 | 5.00 | 5.00 | 5.00 |
| Polyoxyl-40-stearate, NF | 1.00 | 1.00 | 1.00 | 1.00 |
| Cetyl Alcohol, NF | 1.00 | 1.00 | 1.00 | 3.00 |
| Propylparaben, NF | 0.05 | 0.05 | 0.05 | 0.05 |
| Laureth-4 | 1.5 | 1.50 | 1.50 | 1.50 |
| DIMETHICONE 350 | 0 | 0 | 0 | 1.00 |
| Pramoxine HCl, USP | 0 | 1.00 | 1.00 | 1.00 |
| Hydrocortisone Acetate, USP | 1.00 | 0 | 1.00 | 0 |
| Ammonium Lactate, 60%[1] | 24.00 | 24.00 | 24.00 | 21.90 |
| Lactic Acid Concentration | 12.10 | 12.10 | 12.10 | 12.00 |

[1]Actual amount varies depending on the potency of ammonium lactate solution to be equivalent to 12% lactic acid. Ammonium Lactate is a 50%-70% solution, Formulas A through C, calculation is based on 60%. Nominal percentage is shown for Formula D.

Examples 4-6

Multiple Counter Ion Cream Formulations

There preferred formulations, Formulations E-G, of moisturizing creams which, according to the present invention, incorporate ammonium and metal ion salts along with the acid/acid salt composition, are listed in Table 2. These compositions were made using the following procedure:

Hot Water/Active Phase

Water, methylparaben (Napp Technologies, Saddlebrook, Ill.), glycerin 99.5% (Dow Chemical, Midland, Mich.), and propylene glycol (Dow Chemical, Midland, Mich.) were combined and heated with mixing to about 70° C. to about 75° C. in a covered vessel. Active ingredients, such as pramoxine HCl (Abbott Labs, Waukegan, Ill.) or hydrocortisone acetate (Ceres Chemical, White Plains, N.Y.) were optionally added to the hot water phase to provide a but water/active phase.

Oil Phase

Mineral oil (Penreco, Karns City, Pa.), stearic acid (Croda, Parsippany, N.J.), and self-emulsifying wax (POLAWAX. Croda, Parsippany, N.J.) was combined and heated with stirring to about 68° C. to about 72° C.

Emulsion Phase

The hot water/active phase was preferably added to the oil phase when each phase was within the specified temperature range to provide an emulsion. The emulsion was cooled until it reached about 40° C. to about 45° C. The lactate solutions were preferably added and mixing continued until smooth and well blended.

TABLE 2

Percentages by weight

| Ingredient | Formula E | Formula F | Formula G |
|---|---|---|---|
| Water | 52.45 | 45.05 | 45.05 |
| Methylparaben, USP | 0.15 | 0.15 | 0.15 |
| Glycerin 99.5%, USP | 4.0 | 4.0 | 4.0 |
| Propylene Glycol | 5.0 | 5.0 | 5.0 |
| Light Mineral Oil | 10.0 | 10.0 | 10.0 |
| Stearic Acid | 5.0 | 8.0 | 8.0 |
| Self-emulsifying wax (POLAWAX) | 7.0 | 8.0 | 8 |
| Ammonium Lactate, 70% | 5.2 | 5.8 | 5.8 |
| Sodium Lactate, 60% | 5.6 | 6.5 | 6.5 |
| Potassium Lactate, 60% | 5.6 | 6.5 | 6.5 |
| Pramoxine HCl, USP | 0 | 1.0 | 0 |
| Hydrocortisone Acetate, USP | 0 | 0 | 1.0 |
| TOTAL | 100 | 100 | 100 |
| Actual Lactic Acid Concentration | 7.6 | 8.8 | 8.8 |

Examples 7 and 8

Formulation for a Deodorized Lotion and Cream

| Raw Material | Percentage by Weight Lotion | Cream |
|---|---|---|
| Purified water, USP | 49.199 | 48.799 |
| Ammonium lactate solution | 22.00* | 22.00* |
| Light mineral oil, NF | 10.0 | 10.00 |
| Glyceryl stearate (and) PEG-100 stearate | 3.00 | 5.00 |
| Propylene glycol, USP | 5.00 | 5.00 |
| Glycerin, USP 99.5 | 4.00 | 4.00 |
| Laureth-4 | 1.50 | 1.50 |
| Magnesium aluminum silicate, NF | 1.50 | 1.50 |
| Polyoxyl-40-stearate, NF | 1.00 | 1.00 |
| Cetyl alcohol, NF | 0.60 | 1.00 |
| Methylparaben, NF | 0.15 | 0.15 |
| Propylparaben, NF | 0.05 | 0.05 |
| Methylcellulose | 0.001 | 0.001 |

*Deodorized as described below.

Procedure

All raw materials were weighed and the mixer was prepared.

Water Phase

The purified water was heated to about 90° C. to about 95° C. At a moderate mixing speed, the magnesium aluminum silicate (Vanderbilt, Norwalk, Conn.) was added. With continued moderate mixing, the methylcellulose (Dow Chemical, Midland, Mich.) and glycerin (Dow Chemical, Midland, Mich.) were added, maintaining the temperature of about 90° C. to about 95° C. Moderate mixing was continued until the water phase was uniform, at least about 2 minutes, maintaining a temperature of about 90° C. to about 95° C. To this composition the methylparaben (Napp Technologies, Saddlebrook, Ill.) was added, with continued moderate mixing. Mixing was maintained for at least about 10 minutes, until the composition was smooth and homogeneous, while adjusting the temperature to about 80° C. to about 85° C.

Oil Phase (in a Separate Container)

In a separate container, the light mineral oil (Penreco, Karns City, Pa.), the glyceryl stearate and PEG-100 stearate mixture (Uniqema, New Castle, Del.), propylene glycol (Dow Chemical, Midland, Mich.), polyoxyl-40-stearate (Uniqema, New Castle, Del.), cetyl alcohol (Croda, Parsippany, N.J.), propylparaben (Napp Technologies, Saddlebrook, Ill.), and laureth-4 (Uniqema New Castle, Del.) were combined and mixed at low speed, 150 rpm, while they were heated to about 80° C. to about 85° C. until the ingredients were completely melted and the composition was uniform.
Emulsion Phase When the temperatures of both the water and oil phases were at about 80° C. to about 85° C., the oil phase was added to the water phase while mixing at about 270 revolutions per minute (rpm) for about 15 minutes. Mixing was continued at about 102 to about 135 rpm for at least about 45 minutes. The composition was then cooled while mixing at about 141 to about 179 rpm until the temperature of the composition reached 40° C. or below. The ammonium lactate (Pfanstiehl Labs, Waukegan, Ill., or PURAC America, Lincolnshire, Ill.) was then added, and the composition was cooled, with mixing at about 140 to about 165 rpm, until the composition was smooth and uniform, with a final temperature of about 33° C.

Preparation of a Deodorized Composition

In addition to preparing a neutralized acid solution from alpha-hydroxy acid and ammonium hydroxide, such neutralized preparations may be purchased. Nondeodorized ammonium lactate can be purchased from several sources, for example, from PURAC America (Lincolnshire, Ill.). The product is a liquid containing between 58%-64% lactate and 8%-12% ammonium. Lactic acid is produced by fermentation from sugars and is neutralized with ammonium hydroxide to produce ammonium lactate. The method for deodorizing ammonium lactate involves producing a slurry of ammonium lactate with about 30 weight percent per volume of total solution of activated charcoal and mixing for about 30 minutes. The slurry is then filtered to remove the activated charcoal. The resulting solution of ammonium lactate is deodorized. An additional benefit to filtering with activated charcoal is that any impurities that may cause an off color are also removed, leaving a clear solution. The deodorized ammonium lactate is then combined with one or more anesthetic and/or anti-inflammatory agents.

Deodorizing Using an Activated Carbon Cartridge

Using an activated carbon cartridge, one liter of ammonium lactate is passed through the cartridge. The resulting solution has no odor or color.

Deodorizing Using a Slurry

Five hundred kg of activated carbon/charcoal is added to a stainless steel vessel containing 1000 liters of ammonium lactate. The slurry is stainless for a minimum of 30 minutes, then is filtered. The resulting odorless and colorless filtrate is used to prepare creams and lotions.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments awe presented by way of example only with the scope of the invention intended to be limited only by the claims set forth herein as follows.

What is claimed is:

1. A method of treating skin of a subject, the method comprising contacting the subject's skin with a dermatologic composition comprising:
    ammonium lactate in an amount of about 10% to about 15% by weight;
    potassium lactate in an amount of about 3% to about 7% by weight; and
    sodium lactate in an amount of about 3% to about 7% by weight;
wherein the composition has a pH of about 4.5 to about 5.5.

2. The method of claim 1 wherein the dermatologic composition further comprises at least one anti-foaming agent.

3. The method of claim 1 wherein the dermatologic composition further comprises at least one non-ionic surfactant selected from the group consisting of glyceryl stearate, PEG 100-stearate, polyoxyl-20-cetostearyl ether, glyceryl monooleate, glyceryl palmitosterate, self-emulsifying wax, polyoxyl-20-stearate, polyoxyl-40-stearate, polyoxyl-60-stearate, polyoxyl-80-stearate, polyoxyl-20-oleate, polyoxyl-40-oleate, polyoxyl-60-oleate, polyoxyl-80-oleate, polyoxyl-20-palmitate, polyoxyl-40-palmitate, polyoxyl-60-palmitate, polyoxyl-80-palmitate, emulsifying wax, laureth-2, laureth-4, laureth-6, laureth-8, and combinations thereof.

4. The method of claim 1 wherein the dermatologic composition further comprises at least one preservative selected from the group consisting of methyl paraben, ethyl paraben, propyl paraben, propyl paraben sodium salt, propyl paraben potassium salt, butyl paraben, and combinations thereof.

5. The method of claim 4 wherein the preservative is present in the composition in an amount of about 0.02 weight percent to about 1 weight percent.

6. The method of claim 1 wherein the dermatologic composition further comprises at least one humectant selected from the group consisting of glycerin 99.5%, glycerin 95%, glycerin 85%, propylene glycol, butylene glycol, and combinations thereof.

7. The method of claim 6 wherein the humectant is present in the composition in an amount of about 1 weight percent to about 15 weight percent.

8. The method of claim 1 wherein the dermatologic composition further comprises at least one anti-inflammatory agent.

9. The method of claim 8 wherein the at least one anti-inflammatory agent is a corticosteroid.

10. The method of claim 8 wherein the at least one anti-inflammatory agent is selected from the group consisting of hydrocortisone acetate, betamethasone dipropionate, amcinonide, betamethasone valerate, fluocinolone acetonide, triamcinolone acetonide, clocortolone pivalate, dexamethasone, and combinations thereof.

11. The method of claim 1 wherein the dermatologic composition further comprises at least one anesthetic agent.

12. The method of claim 11 wherein the at least one anesthetic agent is selected from the group consisting of pramoxine hydrochloride, benzocaine, benzyl alcohol, dibucaine hydrochloride, dyclonine hydrochloride, lidocaine, tetracaine, and tetracaine hydrochloride.

13. The method of claim 11 wherein the anesthetic agent is pramoxine hydrochloride.

14. A method of treating skin of a subject, the method comprising contacting the subject's skin with a dermatologic composition comprising:

about 10 weight percent to about 15 weight percent of ammonium lactate;
about 3 weight percent to about 7 weight percent of sodium lactate;
about 3 weight percent to about 7 weight percent of potassium lactate;
about 1 weight percent to about 20 weight percent of light mineral oil;
about 2 weight percent to about 10 weight percent of emulsifying wax;
about 1 weight percent to about 5 weight percent of stearic acid;
about 0.01 weight percent to about 1 weight percent of propyl paraben;
about 1 weight percent to about 10 weight percent of glycerin;
about 0.0001 weight percent to about 10 weight percent of xanthan gum;
about 1 weight percent to about 15 weight percent of propylene glycol;
about 0.02 weight percent to about 1 weight percent of methyl paraben; and
about 30% and typically no greater than about 60% by weight of water;
wherein the composition has a pH of about 4.5 to about 5.5.

15. The method of claim 14 wherein the dermatologic composition further comprises at least one anti-inflammatory agent.

16. The method of claim 15 wherein the at least one anti-inflammatory agent is a corticosteroid.

17. The method of claim 15 wherein the at least one anti-inflammatory agent is selected from the group consisting of hydrocortisone acetate, betamethasone dipropionate, amcinonide, betamethasone valerate, fluocinolone acetonide, triamcinolone acetonide, clocortolone pivalate, dexamethasone, and combinations thereof.

18. The method of claim 14 wherein the dermatologic composition further comprises at least one anesthetic agent.

19. The method of claim 18 wherein the at least one anesthetic agent is selected from the group consisting of pramoxine hydrochloride, benzocaine, benzyl alcohol, dibucaine hydrochloride, dyclonine hydrochloride, lidocaine, tetracaine, and tetracaine hydrochloride.

20. The method of claim 19 wherein the anesthetic agent is pramoxine hydrochloride.

* * * * *